United States Patent [19]

Krcma et al.

[11] Patent Number: 5,347,223
[45] Date of Patent: Sep. 13, 1994

[54] GAS LEAK DETECTOR SENSING TIP WITH INTERIOR CONCENTRIC BORES AND CORONA CURRENT GENERATION

[75] Inventors: Jan Krcma, Elk Grove Village; Dennis Martell, Naperville, both of Ill.

[73] Assignee: J and N Associates, Inc., Valparaiso, Ind.

[21] Appl. No.: 7,844

[22] Filed: Jan. 22, 1993

[51] Int. Cl.$^5$ ............... G01N 27/70; G01N 27/60; G08B 21/00
[52] U.S. Cl. ................... 324/455; 324/464; 340/632
[58] Field of Search .......... 324/72, 459, 460, 463–466; 340/632; 436/153, 154; 73/19.01, 23.2, 46.7

[56] References Cited

U.S. PATENT DOCUMENTS

| | | |
|---|---|---|
| 3,237,181 | 2/1966 | Palmer . |
| 3,411,073 | 11/1968 | Marr ................................. 324/463 |
| 3,438,259 | 4/1969 | Bossert, Jr. . |
| 3,460,125 | 8/1969 | Liebermann et al. . |
| 3,559,049 | 1/1971 | Liebermann et al. . |
| 3,728,615 | 4/1973 | Hill et al. . |
| 3,742,475 | 6/1973 | Liebermann et al. . |
| 3,949,390 | 4/1976 | Rayl et al. . |
| 4,488,118 | 12/1984 | Jeffers et al. ..................... 324/455 |
| 4,609,875 | 9/1986 | Jeffers ............................... 324/455 |
| 5,157,333 | 10/1992 | Peacock et al. ............... 324/464 X |

FOREIGN PATENT DOCUMENTS 295020A 10/1991 Fed. Rep. of Germany ...... 324/464
203944 12/1982 Japan .................................. 324/464

Primary Examiner—Gerard R. Strecker
Attorney, Agent, or Firm—Marshall, O'Toole, Gerstein, Murray & Borun

[57] ABSTRACT

A gas leak detector that operates on the corona principle having a sensing tip with a pair of electrodes across which a high voltage is provided to generate a corona current through the electrodes. The sensing tip includes a first electrode having a conductive housing with a first end having a gas inlet formed therein and a second end and a flow passage formed therein. The flow passage has a first bore provided between the gas inlet and the second end of said conductive housing and a second bore having a diameter smaller than that of the first bore. The second bore is provided between the first bore and the gas inlet of the conductive housing and abuts the first bore to form an edge in the interior of the housing. The flow passage also has a third bore of a diameter smaller than that of the second bore provided between the second bore and the gas inlet. The gas leak detector also includes a second electrode provided in the interior of the conductive housing. The second electrode has a tip provided at a defined location with respect to the edge in the interior of said housing. The leak detector also has a voltage supply circuit for generating a voltage sufficient to cause a corona to be formed across the electrodes, with the corona being formed between the second electrode and the edge in the interior of the housing.

25 Claims, 7 Drawing Sheets

GAS LEAK DETECTOR SENSING TIP WITH INTERIOR CONCENTRIC BORES AND CORONA CURRENT GENERATION

BACKGROUND OF THE INVENTION

The present invention is directed to a sensing tip for a gas leak detector for detecting the presence and location of leaks of refrigerant gases such as halogen used in refrigeration systems.

A halogen gas leak detector is disclosed in U.S. Pat. No. 4,488,118 to Jeffers, et al. That detector operates by applying a high voltage across a pair of electrodes provided in a sensing tip to generate a continuous corona current. The magnitude of the corona current varies in response to changes in concentration of halogen gas, and the concentration of gas is determined by sensing changes in the corona current. The sensing tip of the detector, which is shown in FIG. 3 of the Jeffers, et al. patent, incorporates a pointed electrode provided in the interior of a conductive housing having a cylindrical portion terminating in a hemispherical portion. A high voltage is provided across the electrodes to induce a corona current to flow through the electrodes.

A disadvantage of the sensing tip used in the Jeffers, et al. detector is that the corona may form between the pointed electrode and various points on the interior surface of the conductive housing, and may "jump about" by forming between the pointed electrode and a first location on the interior surface of the housing, and then forming between the pointed electrode and a different location on the interior housing surface. As the corona jumps about, the magnitude of the corona current may be affected, so that the magnitude of the corona current will not necessarily reflect accurately the concentration of halogen gas present in the vicinity of the sensing tip. Another disadvantage of the Jeffers, et al. sensing tip is that its particular structure may require an unduly high voltage to be used to generate the corona.

U.S. Pat. No. 4,609,875 to Jeffers discloses a sensing tip for a gas detector having a different structure. The sensing tip, shown in FIG. 4, includes a wire electrode provided within a generally cylindrical outer conductive housing. A conductive tube is provided in the interior of the housing, and the conductive tube is electrically separated from the conductive housing via an insulating tubular casing. A high voltage is provided across the first and second electrodes to induce a corona current to flow through the electrodes.

SUMMARY OF THE INVENTION

The present invention is directed to a gas leak detector apparatus having a sensing tip that operates on the corona principle. The sensing tip has a pair of electrodes across which a high voltage is provided to generate a corona current through the electrodes. The sensing tip has a first electrode with a conductive housing having a first end with a gas inlet formed therein, a second end and a flow passage formed therein. The flow passage has a first bore provided between the gas inlet and the second end of the conducting housing and a second bore of a diameter smaller than the diameter of the first bore. The second bore is provided between the first bore and the gas inlet formed in said conductive housing.

The gas leak detector apparatus has a second electrode provided in the interior of the conductive housing having a tip which is provided at a defined location with respect to the first bore formed in the conductive housing. The detector apparatus also includes a voltage supply circuit for generating a high voltage sufficient to cause a corona to be formed across the first and second electrodes and a conductive member that connects the voltage supply circuit to the second electrode so that said high voltage is provided to the second electrode to form a corona across the first and second electrodes so that a corona current is induced to flow through the electrodes.

The intersection of the first and second bores of the gas flow passage preferably forms an edge, such as a circumferential edge, in relatively close proximity to the second electrode. The edge advantageously presents a well defined conductive point at a well-defined distance from the second electrode so that a relatively stable corona may be formed between the second electrode and the edge, thus resulting in the generation of a relatively stable corona current that does not exhibit changes that are not caused by changes in gas concentration in the vicinity of the sensing tip and also allowing a smaller voltage to be applied across the electrodes to generate the corona.

The gas flow passage formed in the leak detector apparatus preferably includes a relatively narrow bore formed in the conductive housing adjacent the gas inlet. The relatively narrow bore reduces or eliminates the effect which external objects near the vicinity of the sensing tip have on the electric field generated by the high voltage provided across the electrodes and thus results in a more stable corona current.

The conductive housing of the gas leak detector apparatus preferably has structural means for aligning the second electrode with respect to the well-defined conductive edge formed at the intersection of the first and second bores to facilitate the simple and consistent assembly of the sensing tip.

The first and second bores are preferably formed in a unitary portion of the conductive housing so that a relatively simple and reliable construction is provided and which results in a sensing tip that is relatively easy to manufacture and assemble. The gas leak detector apparatus may include one or more filters which advantageously make the sensing tip intrinsically safe and shield the interior of the sensing tip from din and other contaminants during assembly and operation.

These and other features and advantages of the present invention will be apparent to those of ordinary skill in the an in view of the detailed description of the preferred embodiment, which is made with reference to the drawings, a brief description of which is provided below.

DETAILED DESCRIPTION OF A PREFERRED EMBODIMENT

Figure 1:
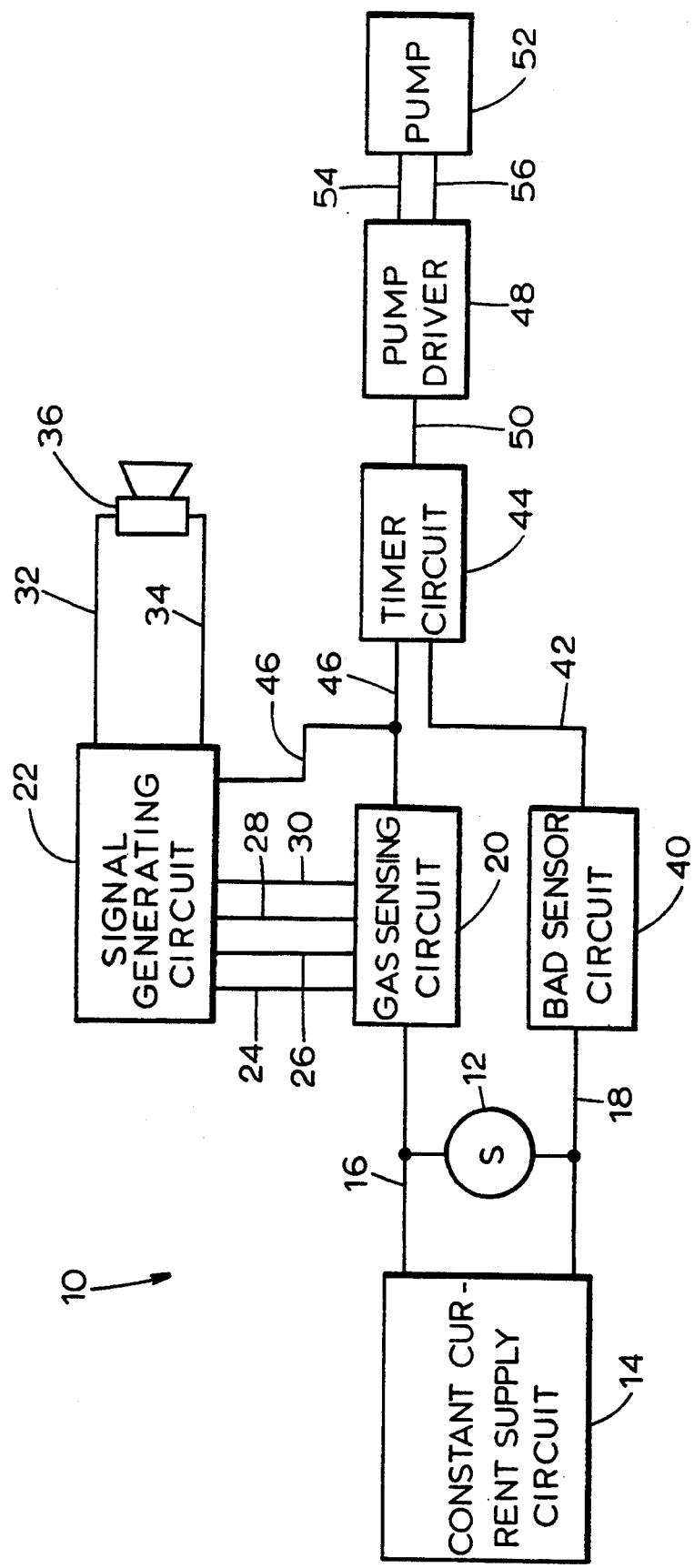
FIG. 1 is a block diagram of the preferred embodiment of the invention.

A preferred embodiment of a refrigerant gas leak detector 10 for detecting the presence and location of leaks of refrigerant gases such as halogen is shown in FIG. 1. The leak detector 10, which is a portable, hand-held detector, has a gas sensing tip 12 which is operated in the continuous corona range. A constant current supply circuit 14, which is connected to the sensing tip 12 via a pair of electrical lines 16, 18, supplies a high variable voltage to the sensing tip 12 such that the corona current through the tip 12 remains substantially constant at all times, regardless of tile concentration of refrigerant gases present. Preferably, the voltage applied to the sensing tip 12 is a high negative voltage.

A gas sensing circuit 20 is connected to tile sensing tip 12 and senses tile voltage on the line 16 connected to the sensing tip 12. The sensed voltage is related to the concentration of refrigerant gas present, with higher voltage magnitudes corresponding to higher concentrations of refrigerant gas. The gas sensing circuit 20 is coupled to a signal generating circuit 22 via four electrical lines 24, 26, 28, 30. In response to the signals generated on the four lines 24–30, the signal generating circuit 22 generates various signals, such as an alarm signal or an abnormal condition signal, that cause various audible and/or visual indications to be generated. When an audible indication is generated, the signal generating circuit 22 drives an audio speaker 36 via a pair of electrical lines 32, 34.

The leak detector 10 also includes a bad sensor circuit 40 coupled to the sensing tip 12 via the line 18. At all times during normal operation of the leak detector 10, a substantially constant corona current of a predetermined magnitude is generated through the sensing tip 12. However, the leak detector circuitry may malfunction or the sensing tip 12 may fail, such as due to excessive aging, causing the sensor current to drop below its predetennined magnitude. In such cases, the bad sensor circuit 40 generates an abnormal condition signal via an electrical line 42 which is coupled to a timer circuit 44. In response to such signal, the timer circuit 44 generates a signal on an electrical line 46 coupled to the signal generating circuit 22 which causes the circuit 22 to generate an abnormal condition signal indicating the presence of an abnormal operating condition.

The timer circuit 44 is also connected to a pump driver circuit 48 via an electrical line 50. The pump driver circuit 48 is used to drive a pneumatic pump 52 via a pair of lines 54, 56. The pump 52 draws the atmosphere in the vicinity of the sensing tip 12 through the tip 12 to facilitate detection of refrigerant gases.

Gas Sensing Tip

Figure 2:
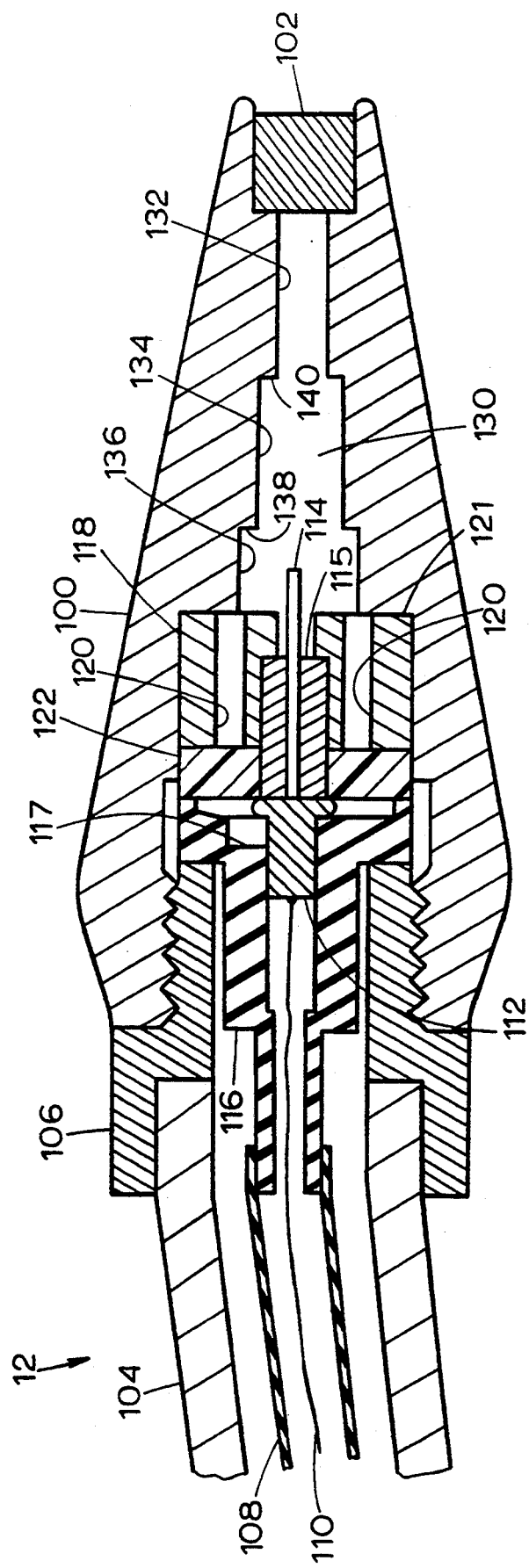
FIG. 2 is a cross-section of the gas sensing tip shown schematically in FIG. 1.

A cross-section of the gas sensing tip 12 is shown in FIG. 2. The sensing tip 12 has a unitary aluminum housing 100 that tapers from a relatively large diameter to a relatively small diameter at its end distal from the main housing (not shown) of the detector 10. A sintered metal filter 102, which allows the passage of gas therethrough, acts as a flame arrestor to make the sensing tip 12 intrinsically safe, and keeps dirt and other foreign matter out of the sensing tip 12, is provided in a gas inlet bore formed in the distal end of the housing 100.

The housing 100 is connected to a length of flexible metal tubing 104 via a steel fitting 106 which has a threaded portion which screws into a threaded interior bore formed in the proximal end of the housing 100. The metal tubing 104 is connected to the main housing of the detector 10. The tubing 104 houses a length of tubing 108 such as rubber tubing in which a high voltage wire 110 is provided. The high voltage wire 110 is electrically connected to a metal rivet 112, which abuts and is electrically connected to a wire electrode 114 anchored in place by a hollow metal tube 115 having a relatively small inside diameter. One end of the tube 115 may crimped (not shown) to anchor the wire electrode 114 firmly within the tube 115. The wire electrode 114 may be a Chromel R type wire commercially available from Hoskins Manufacturing Co.

A nylon support sleeve 116 has a cylindrical extension with a diameter slightly larger than the tubing 108 so that the tubing 108, when forced over the cylindrical extension, is held in place. The cylindrical extension of the sleeve 116 has a central cylindrical bore formed therein to allow the passage of gas therethrough. The support sleeve I 16 has a second internal bore formed therein which is square and slightly larger than the cylindrical bore formed in the cylindrical extension. The cylindrical body of the rivet 112 is press fit in place within the second internal square bore formed in the support sleeve 116. Since the body of the rivet 112 is cylindrical and the bore in which it is provided is square, gas may pass through the square bore when the rivet body is provided therein. The support sleeve 116 has a generally cube-shaped cavity 117 formed therein to facilitate the passage of gas through the sleeve I 16. Without the cavity 117, the head of the rivet 112 may hinder passage of gas through the square bore formed in the support sleeve 116 since the head of the rivet 112 is larger than the cylindrical rivet body.

The metal tube 115 is provided within a central cylindrical bore formed in a generally cylindrical electrode support 118. The internal diameter of the central bore formed in the electrode support 118 decreases at a point to form an annular surface that abuts the end of the tube 115 and retains the tube 115 in place within the electrode support 118. The support 118 has a plurality of circular bores 120 provided along its length to allow for the passage of gas therethrough. The support I 18 may include, for example, six circular bores 120 equally spaced about the circumferential periphery of the support 118.

A porous plastic washer 122 is provided adjacent the electrode support 118. The washer 122 has a central bore in which the tube 115 is provided. The porosity of the washer 122 is sufficient to allow gas to pass therethrough. The washer 122 keeps din and other foreign matter out of the sensing tip 12 during assembly and acts as an additional flame arrestor for intrinsic safety.

The unitary housing 100 of the sensing tip 12 has a gas flow passage 130 formed therein by three coaxial, cylindrical bores each of which has a different diameter. A first bore 132 having the smallest internal diameter is formed closest to the distal end of the sensing tip 12; a second bore 134 having an intermediate internal diameter is formed adjacent the first bore 132; and a third bore 136 having the largest internal diameter is formed adjacent the second bore 134. An annular edge 138 is formed at the intersection of the second and third bores 134, 136, and a second annular edge 140 is formed at the intersection of the first and second bores 132, 134.

The electrode support 118 abuts an annular surface 121 formed in the unitary housing 100 adjacent the end of the third bore 136. Since the annular surface 121 may be performed within the housing 100 at a predetermined distance from the edge 138, and since the tip of the electrode 114 can be positioned to extend a predetermined distance from the electrode support 118, the annular surface 121 acts as a means for aligning the wire electrode 114 so that the tip of the electrode 114 is provided at a fixed location with respect to the edge 138. During assembly of the sensing tip 12, after the electrode I 14 is fixed within the electrode support 118, the electrode 114 is positioned by inserting the support I 18 into the tip 12 until it abuts the annular surface 121. As shown in FIG. 2, the tip of the electrode 114 is positioned so that it is at the approximate horizontal midpoint of the bore 136.

In operation, a high negative voltage generated by the constant current supply circuit 14 is provided to the wire electrode 114 via the line 16, the high voltage wire 110 and the metal rivet 112, and the housing 100 is electrically connected to the line 18 via the steel fitting 106 and the flexible metal tubing 104. Air is drawn via the pump 52 (shown schematically in FIG. 1) through the housing 100 via a flow path through the metal filter 102, the flow passage 130, the bores 120 in the electrode support 118, the porous filter 122, the interior of the support sleeve 116, and the interior of the tubing 108, and the air exits at an aperture (not shown) formed in the metal tubing 104 proximate its connection to the main housing of the leak detector 10.

Due to the large voltage difference between the wire electrode 114 and the housing 100, a corona is formed and a continuous DC corona current flows from the housing 100 to the electrode 114. The presence of refrigerant gas in the air that is passed through the flow passage 130 affects the magnitude of the voltage necessary to keep the corona current substantially constant; thus, the magnitude of the voltage is related to the concentration of refrigerant gas.

The annular edge 138, because it provides a well-defined relatively sharp edge at a well-defined distance from the wire electrode 114, causes a stable corona to be formed between the electrode 114 and the edge 138, as opposed to allowing the corona to be formed between the electrode 114 and some other surface on the interior of the housing 100. As a result of the stable corona, the corona current is also stable and does not exhibit relatively quick magnitude changes that are not caused by changes in the concentration of refrigerant gas present. The provision of the annular edge 138 may increase the life of the sensing tip 12 and may allow a smaller voltage to be used in the sensing tip 12, which would also contribute to enhanced sensing tip life. The use of the relatively narrow bore 132 in the flow passage 130 tends to reduce electric field effects caused by external objects positioned near the sensing tip 12, thus preventing the presence of such external objects from substantially affecting the generated within the sensing tip, and thus the magnitude of the corona current generated.

Constant Current Supply Circuit

Figure 3:
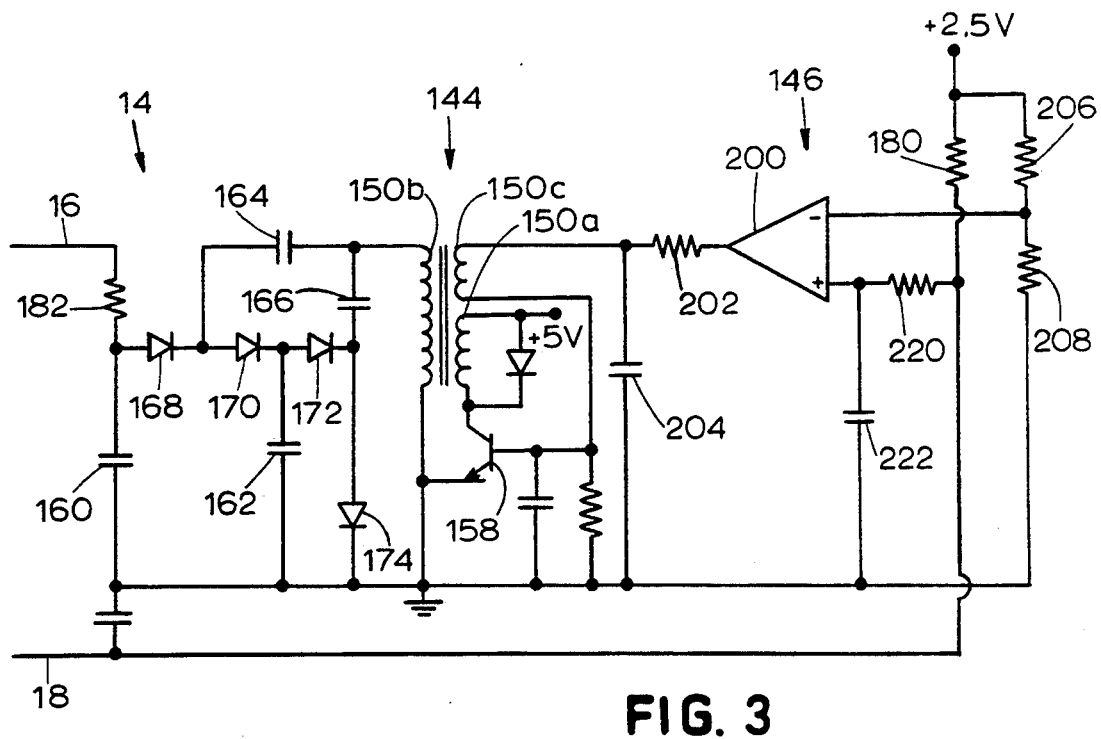
FIG. 3 is a circuit diagram of the constant current supply circuit shown schematically in FIG. 1.

The constant current supply circuit 14, a circuit diagram of which is shown in FIG. 3, includes two basic parts, a voltage supply circuit 144 and a voltage control circuit 146 that controls the voltage supplied by the voltage supply circuit 144 to the sensing tip 12.

Referring to FIG. 3, the voltage supply circuit 144 includes a transformer having a primary winding 150a, a secondary winding 150b and a feedback winding 150c. A transistor 158 provides relatively small amplitude pulses to the primary winding 150a, which induces large amplitude pulses in the secondary winding 150b. The secondary winding 150b is connected to a voltage triplet circuit that includes four capacitors 160, 162, 164, 166 and four diodes 168, 170, 172, 174. The voltage triplet circuit rectifies the high voltage pulses generated by the secondary winding 150b and provides a DC voltage across the lines 16, 18 connected to the sensing tip 12 to generate the corona.

The corona current, which is DC, flows through a current path from a +2.5 volt source, through a resistor 180, across the electrodes via the lines 16, 18, through a resistor 182, and through the diodes 168, 170, 172, 174 to ground.

The magnitude of the corona current is controlled to be substantially constant at all times, regardless of the concentration of refrigerant gas present, by the voltage control circuit 146. The circuit 146 includes an operational amplifier 200 connected to the feedback winding 150c of the transformer via a resistor 202 and a capacitor 204. A reference voltage is provided to the inverting input of the amplifier 200 by its connection to the intersection of a pair of resistors 206, 208 connected in series between a +2.5 volt reference voltage and ground. The noninverting input of the amplifier 200 is connected to sense, through an RC filter circuit comprising a resistor 220 and a capacitor 222, the magnitude of the voltage at the junction of the resistors 180 and 220, which voltage is indicative of the magnitude of the corona current since the corona current flows through the resistor 180. The time constant of the RC filter circuit is small so that only relatively instantaneous signal changes are smoothed.

The amplifier 200 is a very high-gain amplifier that generates an output that is proportional to the difference between the voltage at its noninverting input, which is representative of the magnitude of the corona current, and the reference voltage at its inverting input. The amplifier output is provided to drive the base of the transistor 158. If the voltage representing the corona current is below the reference voltage at its inverting input, the amplifier 200 increases the base drive of the transistor 158 through the feedback winding 150c, thus increasing the magnitude of the pulses in the primary and secondary windings 150a, 150b and increasing the magnitude of the voltage provided to the wire electrode 114 to maintain the corona current at its predetennined level. Due to the voltage control circuit 146, the corona current remains substantially constant at all times during operation of the detector, regardless of the concentration of refrigerant gas present.

Bad Sensor Circuit

Figure 4:
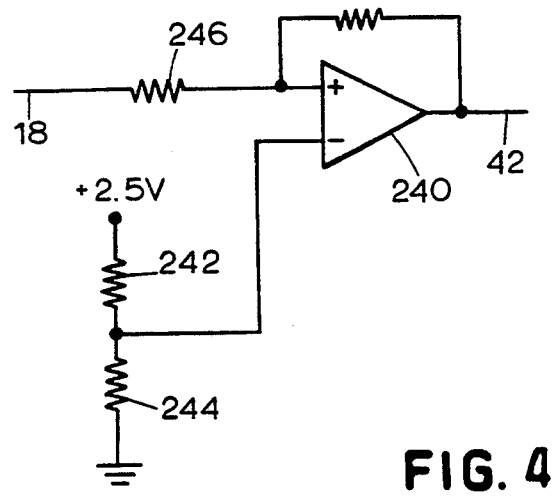
FIG. 4 is a circuit diagram of the bad sensor circuit shown schematically in FIG. 1.

Referring to FIG. 4, a circuit diagram of the bad sensor circuit 40 is shown. The bad sensor circuit 40 can detect a number of abnormal operating conditions and in response generates an abnormal condition signal. Such abnormal conditions may include a defective or worn out sensing tip 12, a sensing tip 12 that is not electrically connected to the leak detector electronics, or a malfunction of the leak detector electronics. Abnormal conditions are assumed to occur when the corona current drops below the substantially constant value to which it should be controlled.

The bad sensor circuit 40 includes a comparator 240 having an inverting input connected to a reference voltage generated at the intersection of a pair of resistors 242, 244 connected in series between +2.5 volts and ground. The comparator 240 compares that reference voltage with the voltage at the junction of the resistors 180 and 220 (FIG. 3), which voltage is representative of the magnitude of the corona current.

It should be appreciated that if the magnitude of the corona current decreases, the voltage on the line 18 will increase, since the resistor 180 (FIG. 3) through which the corona current flows is connected to +2.5 volts. Therefore, magnitude of the reference voltage supplied to the comparator 240 is higher than the reference voltage supplied to the amplifier 200 (FIG. 3) so that the comparator 240 detects when the corona current falls below the value to which it should be controlled. In that case, the voltage on the line 18 would exceed the reference voltage applied to the inverting input of the comparator 120, and the comparator 240 would generate a relatively high output signal, indicating the presence of an abnormal operating condition signal, and would transmit that signal to the timer circuit 44 via the line 42. As described below, the abnormal operating condition signal ultimately causes a red light-emitting diode (LED) to be illuminated.

Timer and Pump Driver Circuits

Figure 5:
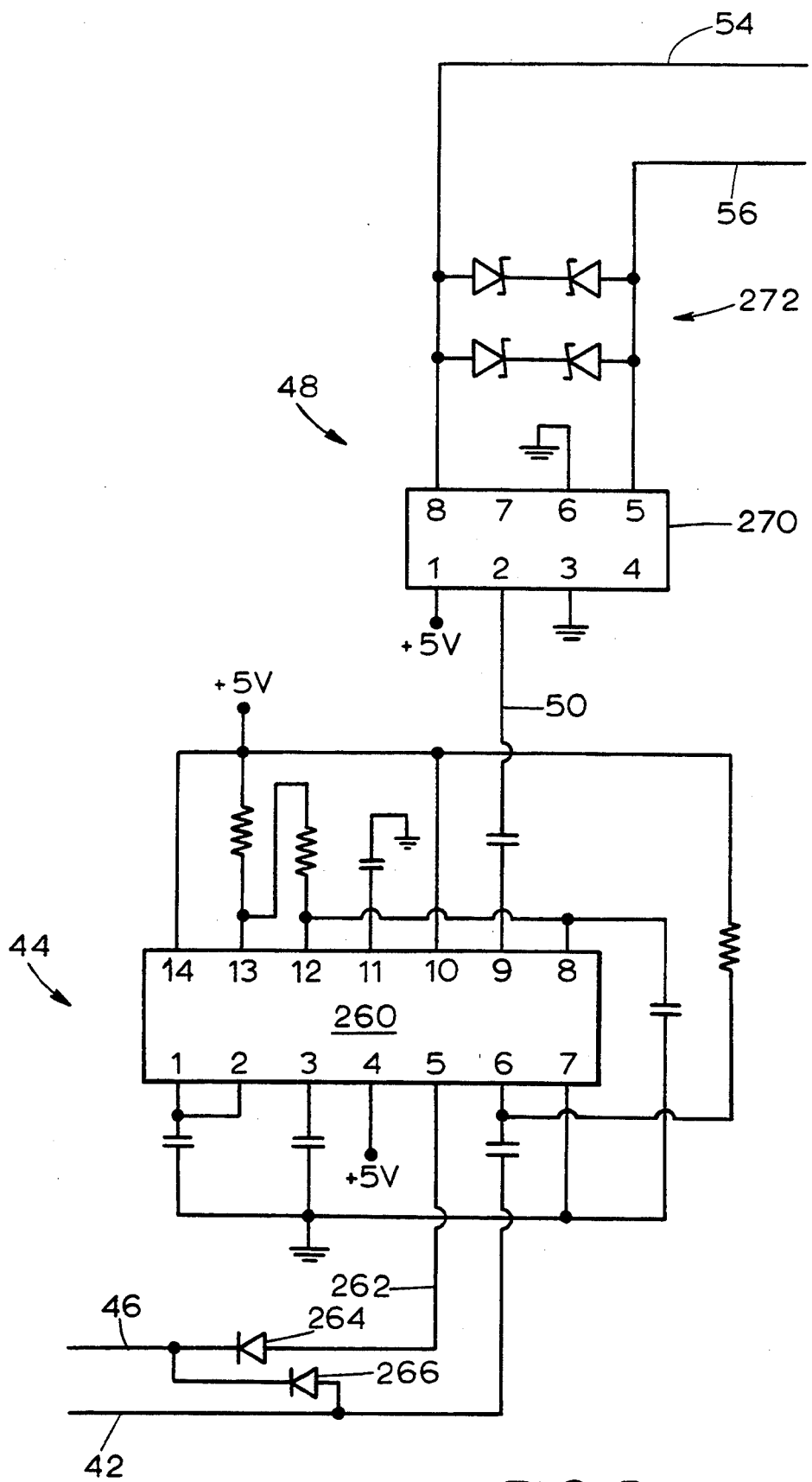
FIG. 5 is a circuit diagram of the timer and pump driver circuits shown schematically in FIG. 1.

A circuit diagram of the timer and pump driver circuits 44, 48 is shown in FIG. 5. The timer circuit 44 includes a conventional integrated circuit 260, such as a well-known '556 circuit, incorporating two timers. One of the timers, which is connected as a retriggerable monostable multivibrator, or one shot, receives the abnormal condition signal generated on the line 42. When that signal becomes active by having a high value, the one shot generates an output signal having a high value on a line 262 that lasts a predetermined period of time. That signal is provided to a diode 264 connected to the line 46. A second diode 266 is connected between the lines 42 and 46. The two diodes 264, 266 act as an OR gate, in that if either signal on the two lines 42, 262 has a high value, the signal on the line 46 also has a high value. When it has a high value, the signal on the line 46, which is supplied to the signal generating circuit 22, causes a red LED 268 (FIG. 7) to be illuminated.

The integrated circuit 260 contains a second timer that generates a constant frequency periodic signal for driving the gas pump 52 (FIG. 1) which draws air through the sensing tip 12. The constant frequency signal is transmitted to a power amplifier circuit 270 via the line 50. The amplifier circuit 270 may be a conventional circuit such as a TDA7052. The amplifier circuit 270 is connected to a zener diode circuit 272, which is connected to the pump 52 via the lines 54, 56.

Gas Sensing Circuit

Figure 6:
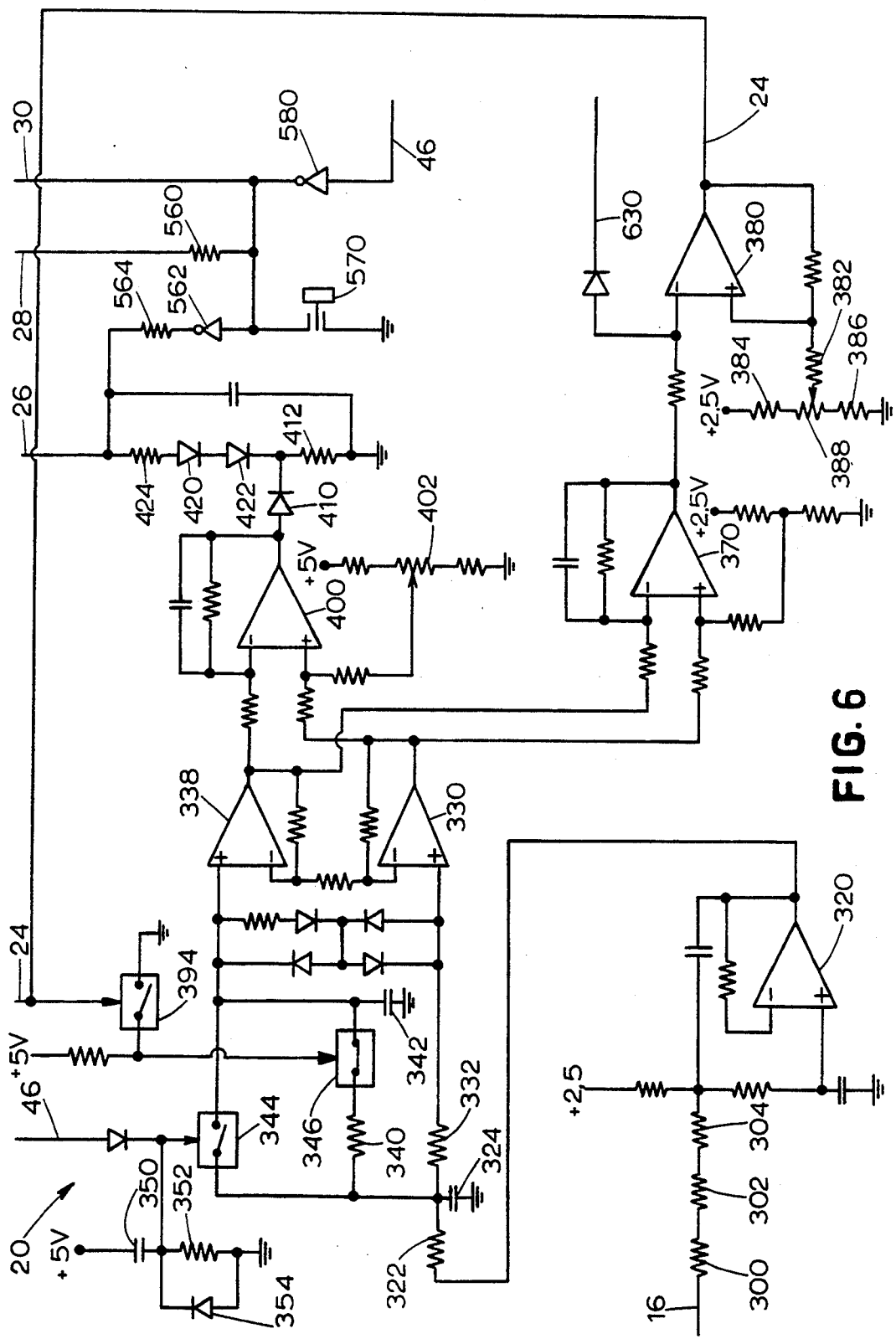
FIG. 6 is a circuit diagram of the gas sensing circuit shown schematically in FIG. 1.

A circuit diagram of the gas sensing circuit 20 is shown in FIG. 6. As described above, the voltage provided to the sensing tip 12 via the line 16 varies with the concentration of refrigerant gas present and is indicative of the amount of such gas present.

Referring to FIG. 6, the gas sensing circuit 20 includes three resistors 300, 302, 304 having very large resistance values connected to detect the voltage on the line 16 connected to the sensing tip 12. The sensing tip voltage signal is filtered by an operational amplifier 320 connected as a low pass filter and by an RC filter circuit including a resistor 322 and a capacitor 324. The sensing tip voltage signal is provided to a first operational amplifier 330 via a resistor 332 and to a second operational amplifier 338 via a variable filter circuit comprising a resistor 340, a capacitor 342, a first, normally open switch 344 and a second, normally closed switch 346 connected in series with the resistor 340.

In normal operation, due to its connection to the variable filter circuit, the operational amplifier 338 acts as a buffer to store a relatively slowly changing signal, the magnitude of which is indicative of the "background" concentration of refrigerant gas present. The operational amplifier 330 acts as a buffer to store a relatively quickly changing signal, the magnitude of which is indicative of the "instantaneous" concentration of refrigerant gas present, which represents the relatively quickly changing concentration of the refrigerant gas, which may be caused by a gas leak.

The time constant of the variable filter circuit varies, depending on the state of the first and second switches 344, 346. The activation terminal of the switch 344 is connected to a switch actuator circuit comprising a capacitor 350, a resistor 352, and a diode 354. Immediately upon power-up of the gas sensing circuit 20, the voltage at the activation terminal of the switch 344 is high, which causes the switch 344 to be in its closed position. In that case, the time constant of the variable filter circuit is relatively fast since the resistor 340 is effectively shorted out. A short time after power is provided to the gas sensing circuit 20, the capacitor 350 becomes charged up, causing the voltage at the activation terminal of the switch 344 to be low, which causes the switch 344 to change to its normally open position. In that case, the variable filter circuit has a relatively long time constant determined by the resistor 340 and the capacitor 342 (the switch 346 is normally closed).

The outputs of the amplifiers 330, 338 are provided to an operational amplifier 370 connected as a difference amplifier that generates a signal representative of the difference between the background signal generated by the amplifier 338 and the instantaneous signal generated by the amplifier 330. The difference signal is provided to an operational amplifier 380 which acts as a comparator. The noninverting input of the amplifier 380 is connected to a reference voltage via a resistor 382. The reference voltage is developed across a pair of resistors 384, 386 and a potentiometer 388 connected in series between ground and +2.5 volts. When the difference voltage provided to the inverting input of the amplifier 380 exceeds the reference voltage provided to the noninverting input, the amplifier 380 generates an alarm signal via the line 24 connected to the signal generating circuit 22. As described below, the alarm signal causes the red LED 268 (FIG. 7) to flash and an audible alarm signal to be sounded.

The line 24 is also connected to the activation terminal of a switch 394, which is in turn connected to the activation terminal of the normally closed switch 346 of the variable filter circuit. When the alarm signal is activated, the switch 394 closes, which causes the normally closed switch 346 to open, thus causing the time constant of the variable filter circuit to be practically infinite since neither of switches 344, 346 is closed and thus the voltage on the capacitor 342 does not change.

The outputs of the amplifiers 330, 338 are also provided to an amplifier 400 connected as a differential amplifier that generates a signal which is provided to the signal generating circuit 22 via the line 26 to generate a ticking sound, similar to that of a Geiger counter, in which the time between the ticks varies according to the concentration of refrigerant gas sensed, with relatively short times between ticks corresponding to relatively high concentrations.

The operation of the amplifier 400 is similar to that of the amplifier 370 previously described. The amplifier 400 generates a difference signal corresponding to the difference between the background refrigerant gas concentration, as determined by the background signal generated by the amplifier 338, and the instantaneous refrigerant gas concentration, as determined by the signal generated by the amplifier 330. The tick rate can be adjusted by the user of the leak detector 10 by adjusting the position of a potentiometer 402 connected to the amplifier 400.

The output of the amplifier 400 is connected to a diode 410 and a resistor 412. A pair of diodes 420, 422 and a resistor 424 are connected in series between the line 26 and the junction of the diode 410 and the resistor 412. The amplifier output signal that appears at the junction of the diode 410 and the resistor 412, referred to herein as the "junction voltage," varies between about zero volts and about +4.4 volts. A junction voltage closer to zero volts corresponds with a relatively large difference between the background and instantaneous refrigerant gas levels, whereas a junction voltage closer to +4.4 volts corresponds with a relatively small difference between the background and instantaneous refrigerant gas levels.

The relationship between the junction voltage and the voltage provided to the signal generating circuit 22 via the line 26, which controls the rate at which the ticking sound is generated, is nonlinear. That nonlinearity is caused by the diodes 420, 422.

As the junction voltage decreases from its maximum value of about +4.4 volts to an intermediate voltage between +4.4 volts and zero volts, the diodes 420, 422 slowly begin to turn on. When the diodes 420, 422 are in the process of turning on, the voltage across each diode varies from between about 0.2 volts to 0.6 volts, and the voltage across each of the diodes 420,422 varies nonlinearly with respect to the current through the each of the diodes 420, 422.

Figure 7:
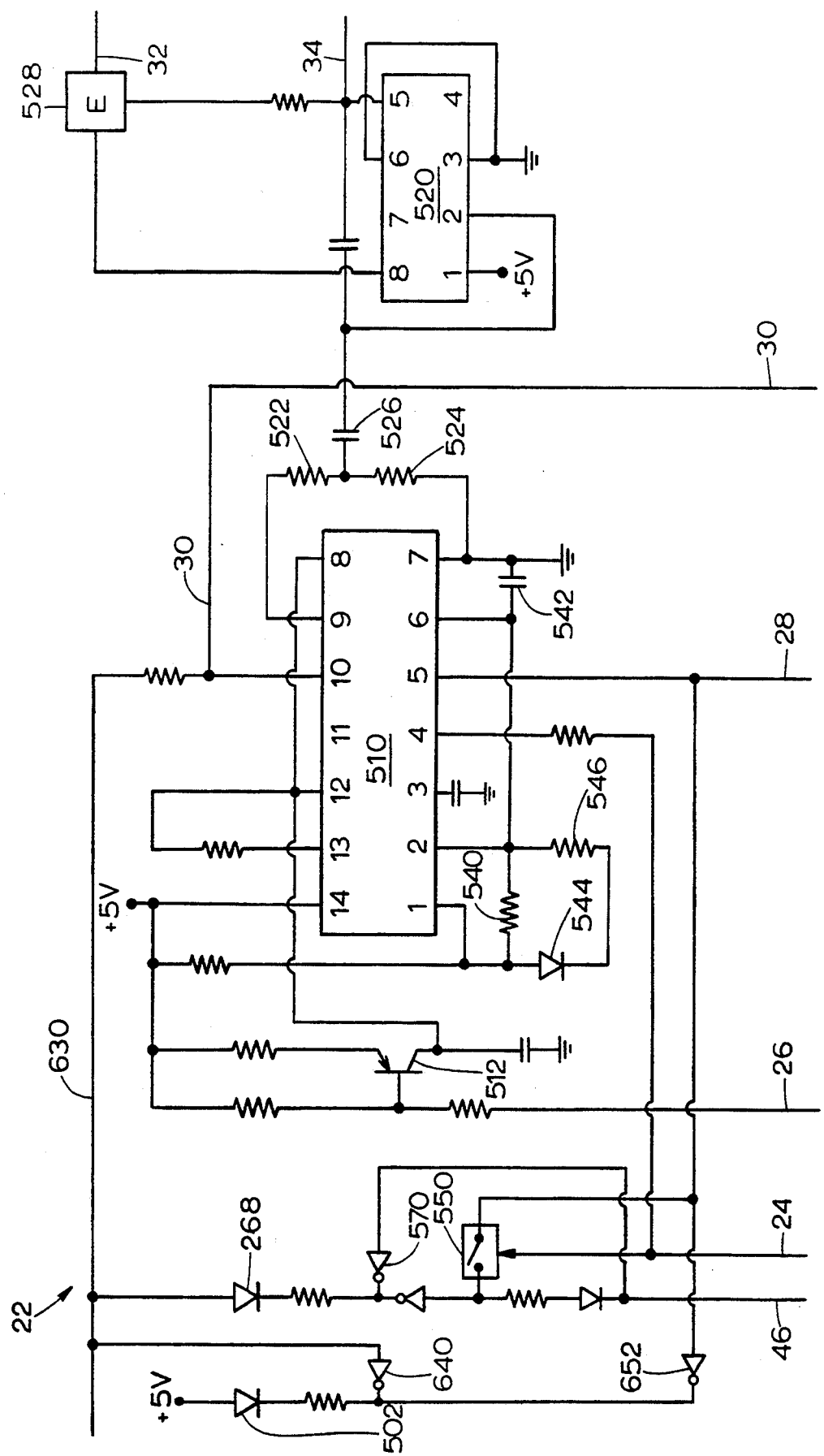
FIG. 7 is a circuit diagram of the signal generating circuit shown schematically in FIG. 1.

When the junction voltage is below the intermediate value between zero and +4.4 volts, the diodes 420, 422 are fully turned on, and the voltage across each of them remains a constant 0.6 volts, regardless of the value of the junction voltage. As a result, when the junction voltage is between the intermediate value and zero volts, the junction voltage varies linearly, and inversely, with respect to the voltage on the line 26, due to the change in voltage across the resistor 424 resulting from the change in the base current of the transistor 512 (FIG. 7).

From the above description, it should be appreciated that the use of the diodes 420,422 causes the gas sensing circuit 22 to have a first sensitivity range, when the junction voltage is above the intermediate voltage, in which the sensitivity of the circuit 22 varies with the junction voltage in a nonlinear fashion, and a second sensitivity range, when the junction voltage is lower than the intermediate voltage, in which the sensitivity of the circuit 22 is constant.

The use of two sensitivity ranges allows the leak detector to detect very small changes in the concentration of refrigerant gas when a low concentration of background refrigerant gas is present, thus allowing the precise location of small gas leaks to be determined, while at the same time being able to detect the location of gas leaks when a high concentration of background refrigerant gas is present. The use of automatically variable sensitivity also negates the need for the user of the leak detector 10 to manually change sensitivity settings.

Signal Generating Circuit

A circuit diagram of the signal generating circuit 22 is shown in FIG. 7. The signal generating circuit 22 generates various audio and visual indications under a number of different conditions. An audio ticking signal is generated during normal operation of the leak detector to generate an indication of the concentration of refrigerant gas present. When an alarm signal is generated on the line 24, meaning that the difference between the background and instantaneous refrigerant gas concentrations is greater than a predetermined value, an audio alarm is generated and the red LED 268 is flashed. When an abnormal condition is detected by the bad sensor circuit 40, the red LED 268 is illuminated constantly. When a low voltage condition is detected by a power supply circuit 500 (FIG. 8) as described in detail below, a green LED 502 is flashed.

Referring to FIG. 7, the signal generating circuit 22 includes an integrated circuit 510, such as a conventional '556 integrated circuit chip, incorporating two timers. One of the timers generates a variable frequency signal that is used to drive the audio speaker 36. The frequency of speaker drive signal is controlled by a transistor 512. The voltage on the line 26 is provided to the base of the transistor 512 and controls the magnitude of the collector current of the transistor 512, which in turn controls the frequency of the speaker drive signal generated by the first timer. When the voltage provided to the base of the transistor 512 is decreased, the base current and collector current increase, thus increasing the frequency of the first timer. The speaker drive signal is transmitted to a conventional driver circuit 520, such as a TDA7052, which drives the speaker 36 via the lines 32, 34, via a pair of resistors 522, 524 and a capacitor 526. An earphone jack 528 may also be provided.

During normal operation, in the absence of an alarm, the speaker drive signal is a variable, relatively low frequency signal which causes a ticking sound to be generated by the speaker 36.

When an alarm signal is generated on the line 24, the other timer contained in the integrated circuit 510 is activated and generates a fixed frequency signal on the line 28. The fixed frequency of the signal is determined by the values of a resistor 540 and a capacitor 542, and the duty cycle of the signal is determined by a diode 544 and the value of a resistor 546. The fixed frequency signal may have a frequency of about two hertz and a duty cycle of about 10%.

The fixed frequency signal is transmitted to a switch 550 connected to the red LED 268 via the line 28 and causes the red LED 268 to flash at the two hertz frequency of the signal. During an alarm, the alarm signal generated on the line 24 causes the switch 550 to be closed so that fixed frequency signal is provided to the red LED 268 to make it flash.

Referring back to FIG. 6, the fixed frequency signal is also provided via the line 28 to a series connection of a resistor 560, an open-collator inverter 562, and a resistor 564 of the gas sensing circuit 20. When the voltage on the line 28 is high, about 10% of the time due to duty cycle of the fixed frequency signal being about 10%, the open-collector inverter 562 generates a low voltage on the line 26, regardless of the voltage at the junction of the diode 410 and resistor 412, causing the base of the transistor 512 (FIG. 7) to be driven hard into conduction, thus causing the variable frequency signal generated by the first timer of the integrated circuit 510 to greatly increase. As a result, during an alarm, when the magnitude of the two hertz fixed frequency signal is high, about 10% of the time, a relatively high frequency alarm tone is generated instead of the low frequency ticking sound. Thus, during an alarm, the ticking sound which is indicative of the refrigerant gas concentration is periodically interrupted for short intervals by a higher frequency alarm. During the remaining 90% of the time, the ticking sound continues to be generate.

The user of the leak detector may prevent the high pitched alarm from interrupting the ticking sound by pressing a pushbutton 570 connected to ground. When the pushbutton 570 is depressed, the input of the inverter 562 is grounded, thus preventing the output of the inverter 562 from generating a low voltage on the line 26 to increase the frequency of the first timer, regardless of the magnitude of the voltage on the line 28.

Referring back to FIG. 7, the signal generating circuit 22 generates an indication signalling the presence of an abnormal operating condition based on the abnormal condition signal generated on the line 46. The line 46 is connected to an inverter 570 connected to the red LED 268. When the voltage on the line 46 is high, indicating the presence of an abnormal condition, the inverter 570 outputs a low voltage, which causes the red LED 268 to be continuously illuminated, since the voltage on the line 630 attached to the opposite end of the LED 268 is normally high.

The abnormal condition signal also causes the audible ticking sound to be disabled. Referring to FIG. 6, the line 46 is connected to an inverter 580 which inverts the voltage of the abnormal condition signal and transmits the inverted signal to the signal generating circuit 22 via the line 30. The inverted signal on the line 30, which is connected to the enable pin (pin 10) of the first timer of the integrated circuit 510, disables the first timer when an abnormal condition is present, thus preventing the speaker 36 from generating any sound.

The line 46 which transmits the abnormal condition signal is also connected to the switch 344 of the variable filter circuit. When an abnormal condition is detected, the signal on the line 46 causes the switch 344 to be closed, thus reducing the time constant of the variable filter circuit, so that a new background gas concentration is stored in the buffer amplifier 338.

The background concentration is reset since an abnormal operating condition typically causes the sensing tip voltage to be artificially high, representing an large concentration of background refrigerant gas. When normal operation resumes, the background concentration will have been just reset.

Power Supply Circuit

Figure 8:
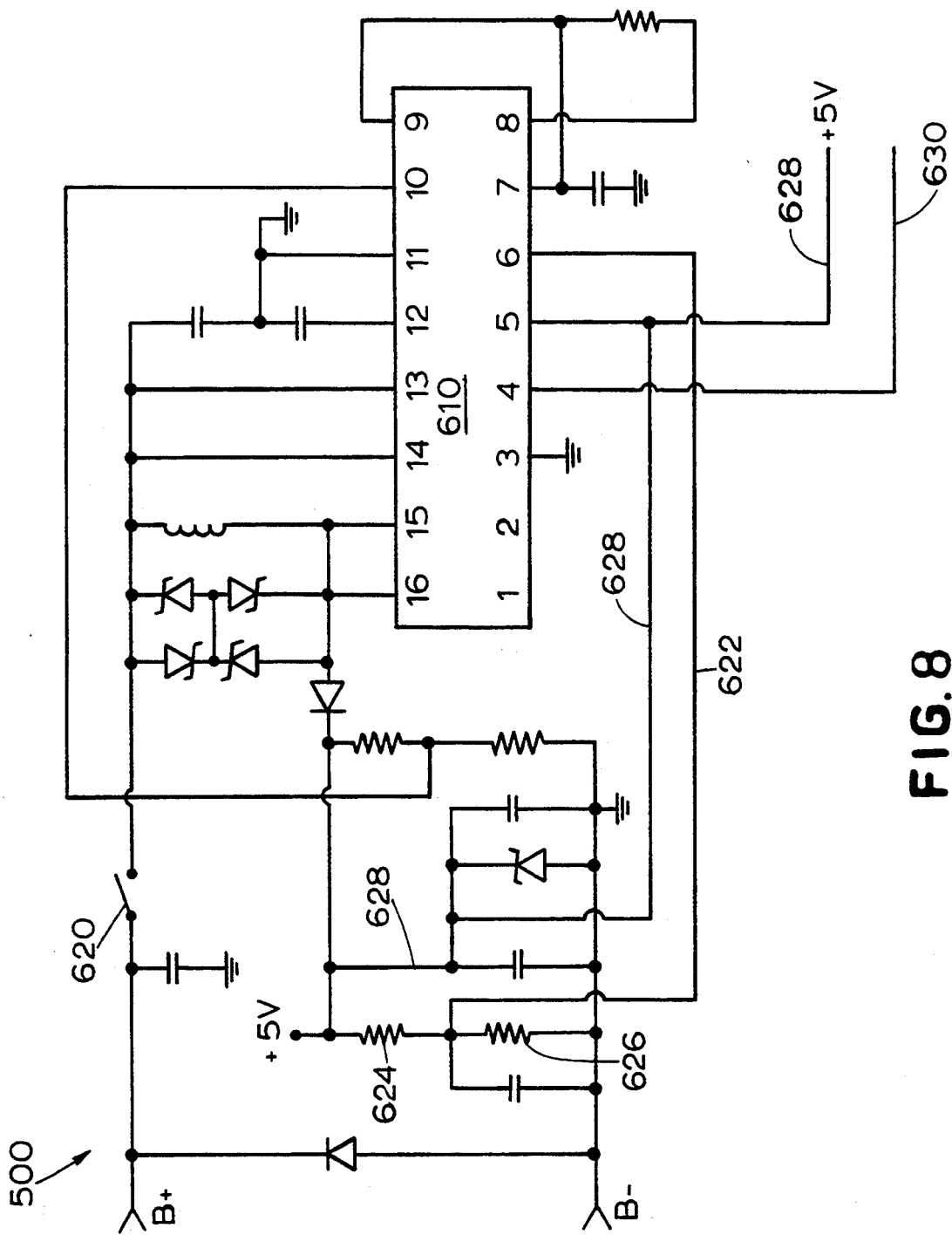
FIG. 8 is a circuit diagram of a power supply circuit usable in the preferred embodiment of the invention.

A circuit diagram of the power supply circuit 500 usable in connection with the preferred embodiment of the invention is shown in FIG. 8. The power supply circuit 500 supplies a voltage of +5 volts to the various circuit components described above. The detailed connections are not shown for purposes of simplicity. The power supply circuit 500 also includes a conventional voltage converter circuit that converts the +5 volts generated by the power supply circuit to +2.5 volts, which is used by a number of circuit components described above.

The power supply circuit 500 also checks the voltage provided by one or more batteries contained in the leak detector. The power supply circuit 500 includes a conventional integrated circuit 610, such as a 78S40. The power supply circuit 500 is connected to a power switch 620 for turning the detector power on and off and a pair of terminals B+ and B− which are connected to one or more batteries (not shown). The circuit 610 includes an internal comparator (not shown) which compares a voltage on a line 622 derived from the voltage supplied by the batteries to the internal reference voltage. The voltage on the line 622 is generated at the junction of a pair of resistors 624, 626 connected in series between +5 volts on a line 628 and ground. Since the +5 volt signal on the line 628 is generated by the integrated circuit 610 from the battery voltage, if the battery voltage sufficiently decreases, so will the +5 volt signal on the line 628. Consequently, the voltage on the line 622 will also decrease and become smaller than the internal reference voltage, and a low battery signal will be generated on a line 630.

The low battery signal has a high value of about +5 volts during normal operation when the batteries are fully charged and a low value when the battery power is weak. Referring to FIG. 7, during normal operation when the batteries are fully charged, the low battery signal having a high value is provided on the line 630 to an inverter 640 coupled to the green LED 502. In that case, the output of the inverter 640 generates a low voltage which will cause the green LED 502 to be continuously illuminated to indicate that the leak detector is operable.

When it changes to a low value, the low battery signal causes the green LED 502 to flash at the two hertz rate of oscillation of the second timer in the integrated circuit 510 (FIG. 7). The low battery signal causes the green LED 502 to flash by inducing the amplifier 380 (FIG. 6), via the line 630 coupled to the noninverting input of the amplifier 380, to generate an alarm signal on the line 24, regardless of the concentration of refrigerant gas present. The alarm signal is provided to the circuit 510 via the line 24 and causes the second timer in the circuit 510 to generate its two hertz, constant frequency signal on the line 28. The oscillating signal on the line 28 is supplied to an inverter 652 connected to the green LED 502 and causes the green LED to flash.

In the absence of an active low battery signal, the oscillating signal on the line 28 would cause the red LED 268 to flash via the connection of the line 28 to the inverter 570 coupled to the red LED 268. To prevent the red LED from flashing, the active low battery signal having a low voltage is provided to the red LED 268 via the line 630, which prevents the red LED 268 from being illuminated due to the low voltage on the line 630.

The active low battery signal on the line 630 also prevents the first timer in the circuit 510 from being enabled due to the connection of the line 630 to the first timer. As a result, the first timer is prevented from generating any driver signal to drive the loudspeaker 36 so that neither a ticking sound nor an audible alarm is generated.

During normal operation of the leak detector when the low battery signal is inactive, its high voltage allows the red LED 268 to be illuminated and enables the timer in the circuit 510 to generate speaker drive signals.

Numerous modifications and alternative embodiments of the invention will be apparent to those skilled in the art in view of the foregoing description. This description is to be construed as illustrative only, and is for the purpose of teaching those skilled in the art the best mode of carrying out the invention. The details of the structure and method may be varied substantially without departing from the spirit of the invention, and the exclusive use of all modifications which come within the scope of the appended claims is reserved.

What is claimed is:

1. A gas leak detector apparatus having a sensing tip that operates on the corona principle, said sensing tip having a pair Of electrodes across which a high voltage is provided to generate a corona current through said electrodes, said sensing tip comprising:
   a first electrode comprising a conductive housing having a first end having a gas inlet formed therein and a second end, said housing having a flow passage formed therein, said flow passage comprising:
   a first bore having a first diameter, said first bore being provided between said gas inlet and said second end of said conductive housing;
   a second bore having a second diameter, said second diameter being smaller than said first diameter of said first bore, said second bore being provided between said first bore and said gas inlet of said conductive housing, said second bore abutting said first bore to form an edge in the interior of said housing; and
   a third bore having a third diameter, said third diameter being smaller than said second diameter of said second bore, said third bore being provided between said second bore and said gas inlet of said conductive housing;
   a second electrode provided in the interior of said conductive housing, said second electrode having a tip being provided at a defined location with respect to said edge in the interior of said housing;
   a voltage supply circuit for generating a high voltage sufficient to cause a corona to be formed across said first and said second electrodes, said corona being formed between said second electrode and said edge in the interior of said housing to generate a relatively stable corona current that does not exhibit substantial magnitude changes in the absence of changes in gas concentration in the vicinity of said sensing tip, said third relatively narrow bore preventing said corona from being substantially affected by the presence of external objects in the vicinity of said sensing tip; and
   means for connecting said voltage supply circuit to said second electrode so that said high voltage is provided to said second electrode to form a corona across said first and said second electrodes so that a corona current is induced to flow through said first and said second electrodes.

2. A gas leak detector apparatus as defined in claim I wherein said means for connecting said voltage supply circuit to said second electrode comprises:
   a conduit attached to said second end of said conductive housing;
   a high voltage wire provided in the interior of said conduit; and
   means for connecting said high voltage wire to said second electrode.

3. A gas leak detector apparatus as defined in claim 2 wherein said means for connecting said high voltage wire to said second electrode comprises a metal rivet.

4. A gas leak detector apparatus as defined in claim 1 additionally comprising a first gas filter provided in said gas inlet formed in said conductive housing.

5. A gas leak detector apparatus as defined in claim 4 wherein said first gas filter comprises a sintered metal block.

6. A gas leak detector apparatus as defined in claim 4 additionally comprising a second gas filter provided in the interior of said conductive housing.

7. A gas leak detector apparatus as defined in claim 6 wherein said second gas filter has a central bore formed therein and wherein said second electrode is provided within said central bore formed in said second gas filter.

8. A gas leak detector apparatus as defined in claim 1 wherein said conductive housing comprises a unitary body.

9. A gas leak detector apparatus as defined in claim 1 wherein said third bore abuts said second bore to form an edge in the interior of said housing.

10. A gas leak detector apparatus as defined in claim 1 wherein said first, second and third bores are cylindrical.

11. A gas leak detector apparatus as defined in claim 1 wherein said second electrode comprises a wire electrode.

12. A gas leak detector apparatus as defined in claim 1 additionally comprising means for supporting said second electrode within said conductive housing.

13. A gas leak detector apparatus as defined in claim 12 wherein said means for supporting said second electrode comprises an electrode support provided adjacent said first bore.

14. A gas leak detector apparatus as defined in claim 13 wherein said electrode support has a body which is cylindrical and through which a plurality of bores are formed to allow the passage of gas through said body.

15. A gas leak detector apparatus as defined in claim 13 wherein said electrode support has a central bore formed therein and wherein said electrode support additionally comprises a conductive tube provided within said central bore of said electrode support, said second electrode being provided within said conductive tube.

16. A gas leak detector apparatus having a sensing tip that operates on the corona principle, said sensing tip having a pair of electrodes across which a high voltage is provided to generate a corona current through said electrodes, said sensing tip comprising:
   a first electrode comprising a conductive housing having a first end having a gas inlet formed therein and a second end, said housing having a flow passage formed therein, said flow passage comprising:
   a first bore having a first diameter, said first bore being provided between said gas inlet and said second end of said conductive housing; and
   a second bore having a second diameter, said second diameter being smaller than said first diameter of said first bore: said second bore being provided between said first bore and said gas inlet formed in said conductive housing:
   a second electrode provided in the interior of said conductive housing, said second electrode having a tip being provided at a defined location with respect to said first bore formed in said conductive housing;

a voltage supply circuit for generating a high voltage sufficient to cause a corona to be formed across said first and said second electrodes: and a conductive member that connects said voltage supply circuit to said second electrode so that said high voltage is provided to said second electrode to form a corona across said first and said second electrodes so that a corona current is induced to flow through said first and said second electrodes.

17. A gas leak detector apparatus as defined in claim 16 additionally comprising a third bore formed in said conductive housing, said third bore being provided between said second bore and said gas inlet of said housing, said third bore having a third diameter less than said second diameter of said second bore to prevent the presence of external objects in the vicinity of said sensing tip from substantially affecting the corona generated within said sensing tip.

18. A gas leak detector apparatus as defined in claim 16 wherein said first and second bores are formed in a unitary conductive portion of said conductive housing.

19. A gas leak detector apparatus as defined in claim 16 wherein said second bore abuts said first bore to form an edge in the interior of said conductive housing, additionally comprising structural means for aligning said second electrode with respect to the interior of said flow passage so that said tip of said second electrode is provided at a fixed location with respect to said edge formed in the interior of said conductive housing.

20. A gas leak detector apparatus having a sensing tip that operates on the corona principle, said sensing tip having a pair of electrodes across which a high voltage is provided to generate a corona current through said electrodes, said sensing tip comprising:

a first electrode comprising a housing having a first end with a gas inlet formed therein and a second end, said housing having a unitary conductive portion in which a flow passage is formed, said flow passage comprising:

a first bore formed in said unitary conductive portion, said first bore having a first diameter, said first bore being provided between said gas inlet and said second end of said conductive housing; and a second bore formed in said unitary conductive portion, said second bore having a second diameter, said second diameter being smaller than said first diameter of said first bore, said second bore being provided between said first bore and said gas inlet formed in said conductive housing, said second bore abutting said first bore to form an edge in the interior of said unitary conductive portion;

a second electrode provided in the interior of said conductive housing, said second electrode having a tip, said tip of said second electrode being provided within said first bore formed in said unitary conductive portion of said housing;

a voltage supply circuit for generating a high voltage sufficient to cause a corona to be formed across said first and said second electrodes; and a conductive member that connects said voltage supply circuit to said second electrode so that said high voltage is provided to said second electrode to form a corona across said first and said second electrodes so that a corona current is induced to flow through said first and said second electrodes.

21. A gas leak detector apparatus as defined in claim 20 additionally comprising structural means for aligning said second electrode with respect to the interior said flow passage so that said tip of said second electrode is provided at a fixed location with respect to said edge formed in the interior of said unitary conductive portion.

22. A gas leak detector apparatus having a sensing tip that operates on the corona principle, said sensing tip having a pair of electrodes across which a high voltage is provided to generate a corona current through said electrodes, said sensing tip comprising:

a first electrode comprising a housing having a first end with a gas inlet formed therein and a second end, said housing having a flow passage is formed, said flow passage comprising:

a first bore having a first diameter, said first bore being provided between said gas inlet and said second end of said conductive housing; and a second bore having a second diameter, said second diameter being smaller than said first diameter of said first bore, said second bore being provided between said first bore and said gas inlet formed in said conductive housing, said second bore abutting said first bore to form an edge in the interior of said conductive housing;

a second electrode provided in the interior of said conductive housing, said second electrode having a tip;

a voltage supply circuit for generating a high voltage sufficient to cause a corona to be formed across said first and said second electrodes: and a conductive member that connects said voltage supply circuit to said second electrode so that said high voltage is provided to said second electrode to form a corona across said first and said second electrodes so that a corona current is induced to flow through said first and said second electrodes, said corona being formed between said second electrode and said edge in the interior of said housing to generate a relatively stable corona current that does not exhibit substantial magnitude changes in the absence of changes in gas concentration in the vicinity of said sensing tip.

23. A gas leak detector apparatus as defined in claim 22 additionally comprising structural means for aligning said second electrode with respect to the interior of said flow passage so that said tip of said second electrode is provided at a fixed location with respect to said edge formed in the interior of said conductive housing.

24. A gas leak detector apparatus as defined in claim 23 wherein said structural means for aligning said second electrode comprises an annular surface formed in the interior of said conductive housing.

25. A gas leak detector apparatus having a sensing tip that operates on the corona principle, said sensing tip having a pair of electrodes across which a high voltage is provided to generate a corona current through said electrodes, said sensing tip comprising:

a first electrode comprising a conductive housing having a first end having a gas inlet formed therein and a second end, said housing having a flow passage formed therein, said flow passage comprising:

a first bore having a first diameter, said first bore being provided between said gas inlet and said second end of said conductive housing; and a second bore having a second diameter, said second diameter being smaller than said first diameter of said first bore, said second bore being provided between said first bore and said gas inlet fondled in said conductive housing;

a second electrode provided in the interior of said conductive housing, said second electrode having a tip being provided at a defined location with respect to said first bore formed in said conductive housing;

a voltage supply circuit for generating a high voltage sufficient to cause a corona to be formed across said first and said second electrodes; and a conductive member that connects said voltage supply circuit to said second electrode so that said high voltage is provided to said second electrode to form a corona across said first and said second electrodes so that a corona current is induced to flow through said first and said second electrodes, the relatively small diameter of said second bore preventing the presence of external objects in the vicinity of said sensing tip from substantially affecting the corona generated within said sensing tip.

* * * * *

UNITED STATES PATENT AND TRADEMARK OFFICE
CERTIFICATE OF CORRECTION

PATENT NO. : 5,347,223

DATED : September 13, 1994

INVENTOR(S) : Jan Krcma, Dennis Martell

It is certified that error appears in the above-identified patent and that said Letters Patent is hereby corrected as shown below:

Column 2, line 47 "din" should be --dirt--

Column 2, line 51 "the an in" should be --the art in--

Column 3, line 18 "tile" should be --the--

Column 3, line 21 "tile" should be --the--

Column 3, line 22 "tile" should be --the--

Column 3, line 45 "predetennined" should be --predetermined--

Column 4, line 25 "l16" should be --116--

Column 4, line 35 "l16" should be --116--

Column 4, line 48 "l18" should be --118--

Column 4, line 56 "din" should be --dirt--

Column 5, line 6 "performed" should be --preformed--

Column 5, line 14 "l14" should be --114--

Column 5, line 16 "l18" should be --118--

Column 5, line 62 "the generated" should be --the corona generated--

Column 6, line 10 "triplet" should be --tripler--

UNITED STATES PATENT AND TRADEMARK OFFICE
CERTIFICATE OF CORRECTION

PATENT NO. : 5,347,223

DATED : September 13, 1994

INVENTOR(S) : Jan Krcma, Dennis Martell

It is certified that error appears in the above-identified patent and that said Letters Patent is hereby corrected as shown below:

Column 6, line 12 "triplet" should be --tripler--

Column 6, line 53 "predetennined" should be --predetermined--

Column 10, line 67 "open-collator" should be --open collector--

Column 11, line 17 "generate" should be --generated--

Column 14, line 63 "bore:" should be --bore,--

Column 14, line 65 "housing:" should be --housing;--

Column 15, line 5 "electrodes:" should be --electrodes;--

Column 16, line 35 "electrodes:" should be --electrodes;--

Column 17, line 8 "fondled" should be --formed--

Signed and Sealed this

Twenty-first Day of March, 1995

Attest:

BRUCE LEHMAN

*Attesting Officer*  *Commissioner of Patents and Trademarks*